(12) United States Patent
Kobayashi

(10) Patent No.: US 12,207,791 B2
(45) Date of Patent: Jan. 28, 2025

(54) ENDOSCOPE DEVICE

(71) Applicant: HOYA CORPORATION, Tokyo (JP)

(72) Inventor: Takahiro Kobayashi, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 387 days.

(21) Appl. No.: 17/775,044

(22) PCT Filed: Nov. 24, 2020

(86) PCT No.: PCT/JP2020/043580
§ 371 (c)(1),
(2) Date: May 6, 2022

(87) PCT Pub. No.: WO2021/111920
PCT Pub. Date: Jun. 10, 2021

(65) Prior Publication Data
US 2022/0395161 A1 Dec. 15, 2022

(30) Foreign Application Priority Data
Dec. 4, 2019 (JP) ................................. 2019-219332

(51) Int. Cl.
*A61B 1/00* (2006.01)
*A61B 1/012* (2006.01)
(52) U.S. Cl.
CPC .......... *A61B 1/00131* (2013.01); *A61B 1/012* (2013.01); *A61B 1/0008* (2013.01)
(58) Field of Classification Search
None
See application file for complete search history.

(56) References Cited

U.S. PATENT DOCUMENTS 3,897,775 A * 8/1975 Furihata ............. A61B 1/00066
600/146
2002/0099265 A1* 7/2002 Wako ....................... A61B 1/07
600/132

(Continued)

FOREIGN PATENT DOCUMENTS

CN 108348139 A 7/2017
EP 3 082 563 A1 10/2016

(Continued)

OTHER PUBLICATIONS

International Search Report (ISR) dated Jan. 19, 2021 filed in PCT/JP2020/043580.

(Continued)

*Primary Examiner* — John P Leubecker
*Assistant Examiner* — Jae Woo
(74) *Attorney, Agent, or Firm* — GREENBLUM & BERNSTEIN, P.L.C.

(57) ABSTRACT

Provided is an endoscope device capable of enhancing mechanical strength and durability against various operations and attachment to and detachment from a hanger in the endoscope device in which an endoscope can be suspended on the hanger. This endoscope device includes: an insertion portion; an operation unit that has a joint section configured to be suspendable from a hanger and is connected to the hanger through the joint section; a treatment tool channel that is arranged inside the joint section and the operation unit and allows passage of a treatment tool; a plate fixed to the operation unit; and a frame that is provided inside the joint section, includes a plurality of partition structural members coupled to each other and having a longitudinal direction along an arrangement direction of the treatment tool channel, and is fixed to the plate.

8 Claims, 9 Drawing Sheets

(56) References Cited

U.S. PATENT DOCUMENTS

| | | | |
|---|---|---|---|
| 2004/0267089 A1* | 12/2004 | Otsuka | A61B 1/00188 600/102 |
| 2007/0238927 A1* | 10/2007 | Ueno | A61B 1/00105 600/152 |
| 2008/0009672 A1* | 1/2008 | Krattiger | A61B 1/063 600/112 |
| 2008/0132755 A1* | 6/2008 | Kanazawa | A61B 90/50 600/102 |
| 2010/0095969 A1* | 4/2010 | Schwartz | A61B 1/00052 128/207.14 |
| 2012/0184814 A1* | 7/2012 | Ebata | A61B 1/00105 600/109 |
| 2013/0034825 A1* | 2/2013 | Phillips | A61B 1/00183 433/29 |
| 2017/0007106 A1* | 1/2017 | Koyama | A61B 1/0051 |
| 2017/0105603 A1* | 4/2017 | Hosaka | A61B 1/00052 |
| 2017/0150870 A1* | 6/2017 | Koyama | A61B 1/018 |
| 2017/0215697 A1* | 8/2017 | Hatano | A61B 1/0052 |
| 2017/0273545 A1* | 9/2017 | Dong | A61B 1/00029 |
| 2017/0332882 A1* | 11/2017 | Yamamoto | A61B 1/0016 |
| 2017/0336579 A1* | 11/2017 | Sanandajifar | G02B 6/406 |
| 2018/0309908 A1* | 10/2018 | Matthison-Hansen | A61B 1/00066 |
| 2018/0375236 A1* | 12/2018 | Arakawa | H01R 12/732 |
| 2019/0053861 A1* | 2/2019 | Lwin | A61B 1/005 |
| 2019/0142254 A1* | 5/2019 | Chiba | A61B 1/000095 600/109 |
| 2019/0246877 A1* | 8/2019 | Mitsuya | A61B 1/00066 |
| 2020/0253460 A1* | 8/2020 | Yoshinaga | A61B 1/0125 |
| 2020/0315720 A1 | 10/2020 | Lwin et al. | |
| 2020/0359877 A1* | 11/2020 | Seow | A61B 1/00121 |
| 2022/0192475 A1* | 6/2022 | Montero González | A61B 1/0055 |
| 2022/0241035 A1 | 8/2022 | Yamamoto et al. | |

FOREIGN PATENT DOCUMENTS

| | | |
|---|---|---|
| JP | 11-225941 A | 8/1999 |
| JP | 2007-68708 A | 3/2007 |
| JP | 2008-272299 A | 11/2008 |
| JP | 2010-162274 A | 7/2010 |
| JP | 2018-509267 A | 4/2018 |
| WO | 2016/148642 A1 | 9/2016 |
| WO | 2019/087549 A1 | 5/2019 |

OTHER PUBLICATIONS

Supplementary European Search Report issued in European application 20895170.7, dated Nov. 6, 2023.

* cited by examiner

ENDOSCOPE DEVICE

TECHNICAL FIELD

The present invention relates to an endoscope device, and more particularly to an endoscope device configured such that an endoscope can be suspended on a hanger.

BACKGROUND ART

In the field of endoscopes, an endoscope device including a treatment tool (robot treatment tool) configured to be remotely operable is known. The treatment tool is controlled by a physician in a master system located at a distance from an endoscope. The treatment tool inserted into the endoscope operates according to the content of control by the master system.

For example, Patent Literature 1 describes an endoscopic surgery system as follows.

(1) An endoscope using a treatment tool, which can be remotely operated, is provided with a joint section in an operation unit thereof.

(2) The endoscopic surgery system using the treatment tool, which can be remotely operated, includes a dedicated hanger on which the endoscope can be suspended. The dedicated hanger has a connector unit attachable to and detachable from the joint section. The joint section is attachable to and detachable from the dedicated hanger through the connector unit.

(3) Since the endoscope is mounted on the dedicated hanger through the joint section during surgery, it is unnecessary for an operator to keep holding the endoscope during the surgery, and it is possible to reduce fatigue of the operator and to perform a stable endoscopic surgery.

(4) The treatment tool that can be remotely operated is controlled by a master and slave system.

However, there is a case where it is necessary to use the operation unit of the endoscope suspended on the dedicated hanger by rotating and swaying the operation unit in order to secure the field of view observed by the endoscope at the time of performing the surgery using the treatment tool. Since a mechanical load is applied to the joint section due to such rotation or sway, the joint section provided in the operation unit of the endoscope is required to have mechanical strength suitable for each operation.

In addition, in this endoscopic surgery system, it is necessary to connect the joint section provided in the operation unit of the endoscope to the dedicated hanger for use every surgery, and thus, the joint section provided in the operation unit of the endoscope is required to have such mechanical strength as to be capable of withstanding such repeated attachment and detachment.

CITATION LIST

Patent Literature

Patent Literature 1: JP 2018-509267 A

SUMMARY OF INVENTION

Technical Problem

An object of the present invention is to provide an endoscope device capable of enhancing mechanical strength and durability against attachment to and detachment from a hanger and various endoscopic operations at the time of connection to the hanger in the endoscope device in which an endoscope can be suspended on the hanger.

Solution to Problem

In order to solve the above problem, an endoscope device according to the present invention includes: an insertion portion; an operation unit that has a joint section configured to be suspendable on a hanger and is connected to the hanger through the joint section; a treatment tool channel that is arranged inside the joint section and the operation unit and allows passage of a treatment tool; a plate fixed to the operation unit; and a frame that is provided inside the joint section, includes a plurality of partition structural members coupled to each other and having a longitudinal direction along an arrangement direction of the treatment tool channel, and is fixed to the plate.

Advantageous Effects of Invention

According to the endoscope of the present invention, it is possible to provide the endoscope device capable of enhancing mechanical strength and durability against attachment to and detachment from the hanger and various endoscopic operations at the time of connection to the hanger in the endoscope device in which the endoscope can be suspended on the hanger.

DESCRIPTION OF EMBODIMENTS

Hereinafter, the present embodiment will be described with reference to the accompanying drawings. In the accompanying drawings, functionally identical elements may be represented by the same number. Note that the accompanying drawings illustrate the embodiment and implementation examples conforming to the principles of the present disclosure, but these are provided to aid in understanding the present disclosure and should not be interpreted as limiting the present disclosure. The description in this specification is merely exemplary and is not intended to limit the scope of the claims or application examples of the present disclosure in any significance.

The present embodiment will be described in such sufficient detail as to enable those skilled in the art to carry out the present disclosure. However, it is necessary to understand that other implementations and modes are also possible, and that various modifications of configurations and structures and substitutions of various elements are possible without departing from the scope and spirit of the technical concepts of the present disclosure. Therefore, the following description should not be interpreted as being limited thereto.

Figure 1:
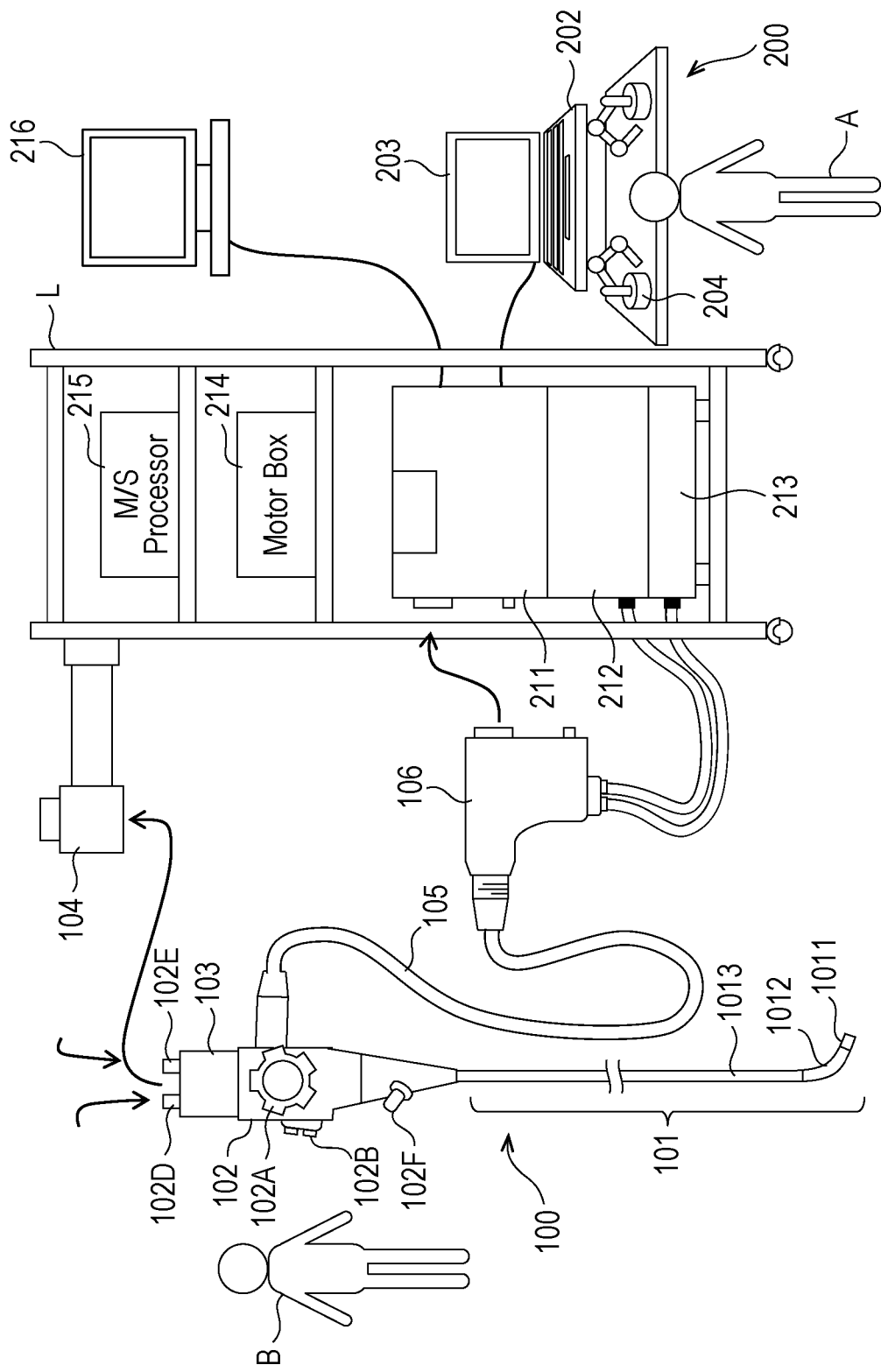
FIG. 1 is a schematic diagram illustrating an overall configuration of an endoscopic surgery system according to an embodiment of the invention.

An overall configuration of an endoscopic surgery system (endoscope device) according to the embodiment of the invention will be described with reference to FIG. 1. This endoscopic surgery system generally includes an endoscope 100 and a master system 200.

The endoscope 100 is an imaging device that captures an image of a portion to be examined by inserting an insertion portion into the body of the subject, and is configured to enable various treatment tools to be inserted therein as will be described later. The treatment tools include a manual treatment tool and a robot treatment tool (manipulator). The manual treatment tool is a treatment tool used for a general endoscope (for example, a treatment tool used in general endoscopic surgery such as hemostasis or local injection), and can be inserted from a treatment tool insertion port 102F to be described later. On the other hand, the robot treatment tool (manipulator) is a treatment tool (slave) controlled by a controller 204 of the master system 200 to be described later. The robot treatment tool can be inserted from a treatment tool insertion port 102D or 102E to be described later.

The endoscope 100 includes an insertion portion 101, a hand operation unit 102, a universal cable 105, and a connector unit 106. The insertion portion 101 further includes a distal tip 1011, a bending section 1012, and a flexible tube section 1013. The hand operation unit 102 includes a joint section 103.

The distal tip 1011 is provided at an end portion of the insertion portion 101, includes an image sensor therein, and includes end portions of various channels. In addition, the bending section 1012 is configured to be actively bendable by operating a bending adjustment knob 102A of the hand operation unit 102. In addition, the flexible tube section 1013 is a portion that is passively bendable by an external force regardless of the operation of the hand operation unit 102.

The flexible tube section 1013 is connected to the hand operation unit 102 at one end thereof. The hand operation unit 102 includes, for example, the bending adjustment knob 102A and an operation button 102B, and causes an operator to perform various operations for observation and imaging by the endoscope 100.

The joint section 103 forms a part of the hand operation unit 102, and is a connection member configured to be connectable to a hanger 104 (to be described later) in a suspended state and to be connected to the hand operation unit 102 in order to suspend the endoscope 100. Details of a structure of the joint section 103 will be described later.

Note that the joint section 103 and a case 102C include treatment tool insertion ports 102D to 102F for the insertion of the treatment tool.

Note that, for example, a structure as disclosed in JP 2018-509267 A can be adopted as a specific structure of a connecting portion between the joint section 103 and the hanger 104.

The universal cable 105 extends from the opposite side of the hand operation unit 102 toward the connector unit 106. The universal cable 105 includes a light guide, various wirings, and various channels therein similarly to the insertion portion 101. The connector unit 106 includes various connectors for connecting the endoscope 100 to a processor 211 to be described later.

As an example, the master system 200 includes an input device 202, a display 203, and a controller 204. As an example, the master system 200 can also be operated by a physician A who operates the hand operation unit 102 while gripping the endoscope 100 and is different from an endoscopist B.

Although not illustrated in detail, the controller 204 is configured by a combination of a lever, a button, a foot pedal, and the like as an example, and is operated by the physician A for operating, positioning, and the like of a robot treatment tool in the endoscope 100. The endoscopist B holds the endoscope 100, and executes the operation of the hand operation unit 102 and the operation of the insertion portion 101 so as to move the distal tip 1011 of the endoscope 100 to a desired position according to an instruction of the physician A. The physician A operates the controller 204 to execute the operation of the robot treatment tool based on an image captured by the endoscope 100 and displayed on the display 203.

The endoscopic surgery system includes the processor 211, an air/water supply unit 212, a suction unit 213, a motor box 214, a master slave system processor 215, a display 216, and the like.

The processor 211 receives an image signal from the endoscope 100 and performs predetermined signal processing. The processor 211 may include a light source, which emits irradiation light for irradiation of an object, therein. The air/water supply unit 212 performs control to release a water flow or an air flow supplied to the subject. The suction unit 213 includes a pump and a tank (not illustrated) for suction of body fluid and an excised material sucked from a body of the subject through the endoscope 100.

The motor box 214 stores various motors configured to generate a driving force for driving the robot treatment tool of the endoscope 100. The various motors operate based on drive signals generated in accordance with control signals transmitted from the master system 200. The master slave system processor 215 executes various types of control on the robot treatment tool through the motor box 214 according to instructions from the master system 200. The display 216 is a display device configured to perform display based on, for example, a data processing result in the processor 211.

The processor 211, the air/water supply unit 212, the suction unit 213, the motor box 214, and the master slave system processor 215 are stored in a rack L. The rack L further includes the hanger 104 that is connected to the joint section 103 to suspend the endoscope 100.

A structure of the distal tip 1011 of the endoscope 100 will be described with reference to FIG. 2. Light distribution lenses 112A and 112B are arranged at the distal tip 1011 of the endoscope 100, and light guides LGa and LGb extend from the distal tip 1011 to the connector unit 106 inside the insertion portion 101. Light from a light source device in the processor 211 is guided by the light guides LGa and LGb, and is emitted toward the subject by the light distribution lenses 112A and 112B arranged at the distal tip 1011.

Figure 2:
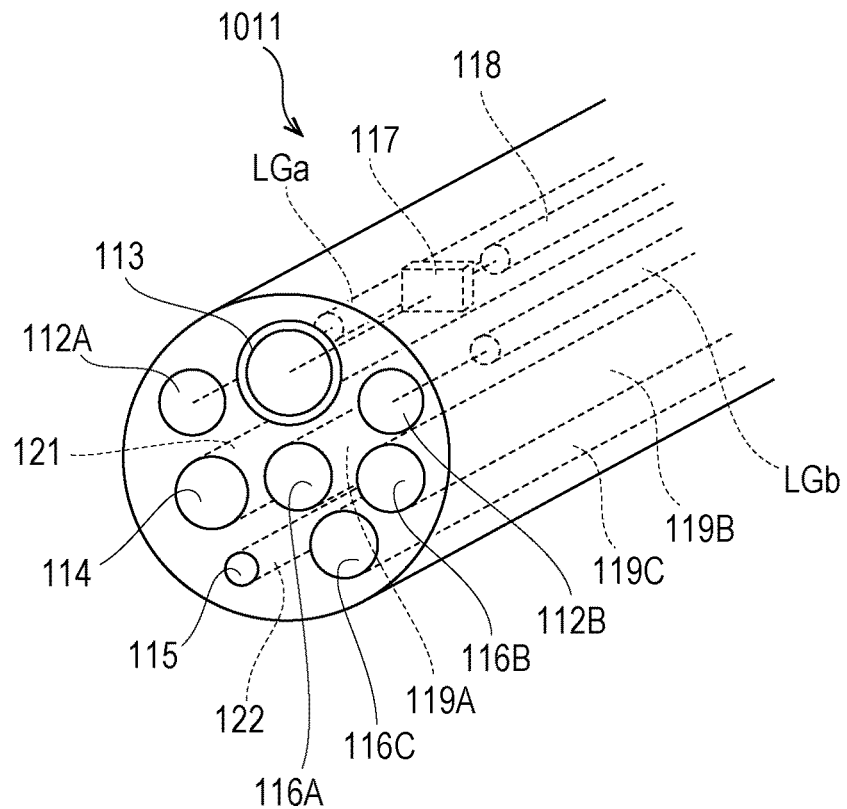
FIG. 2 is a schematic perspective view illustrating a structure of a distal tip 1011 of an endoscope 100.

In addition, the endoscope 100 includes an objective lens 113 and an image sensor 117 at the distal tip 1011 as illustrated in FIG. 2. The objective lens 113 provided at the distal tip 1011 collects scattered light or reflected light from the subject to form an image of the subject on a light receiving surface of the image sensor 117.

The image sensor 117 can be configured using, for example, a charge coupled device (CCD) or a complementary metal oxide semiconductor sensor (CMOS Sensor). The image sensor 117 is controlled by a signal (a gain control signal, an exposure control signal, a shutter speed control signal, and the like) supplied from the processor 211 through an electrical wiring 118, and supplies an image signal of a captured image to the processor 211 through the electrical wiring 118 and an A/D conversion circuit (not illustrated).

In addition, an air/water supply port 114, an auxiliary water supply port 115, and treatment tool ports 116A to 116C are provided, as end portions or openings of various channels, on an end surface of the distal tip 1011. The air/water supply port 114 is connected to an air/water supply channel 121 to introduce a water flow or an air flow for cleaning or the like of the distal tip 1011.

In addition, the auxiliary water supply port 115 is connected to an auxiliary water supply channel 122 in order to introduce auxiliary water supply for removal of wastes in the field of view. The channels 121 and 122 are arranged to extend along the inside of each of the distal tip 1011, the bending section 1012, the flexible tube section 1013, the hand operation unit 102, and the universal cable 105.

The treatment tool channels 119A to 119C are provided inside the endoscope 100, in addition to these channels 121 and 122. The treatment tool channels 119A to 119C are arranged inside the hand operation unit 102 and/or the joint section 103 so as to allow a treatment tool such as forceps to pass therethrough while freely moving back and forth. Distal tips of the treatment tool channels 119A to 119C form the treatment tool ports 116A to 116C, respectively, at the distal tip 1011. In addition, two of the treatment tool channels 119A to 119C communicate with the treatment tool insertion ports 102D and 102E, respectively, and the remaining one thereof communicates with the treatment tool insertion port 102F and is also used as a suction channel. Note that at least one of the treatment tool channels 119A to 119C may also serve as the suction channel.

Figure 3:
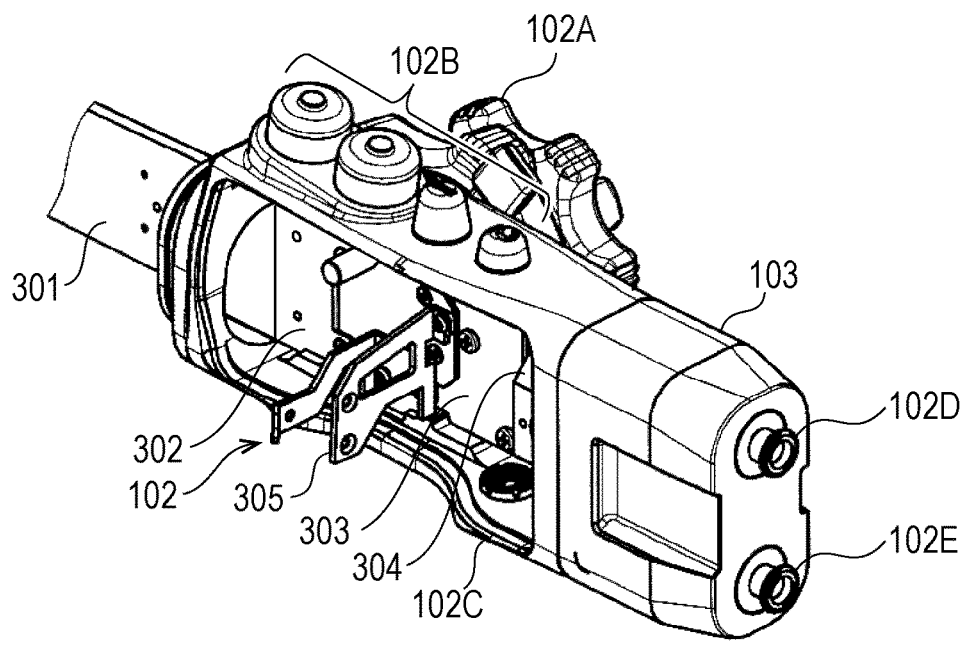
FIG. 3 is a perspective view illustrating details of structures of a hand operation unit 102 and a joint section 103.
Figure 4:
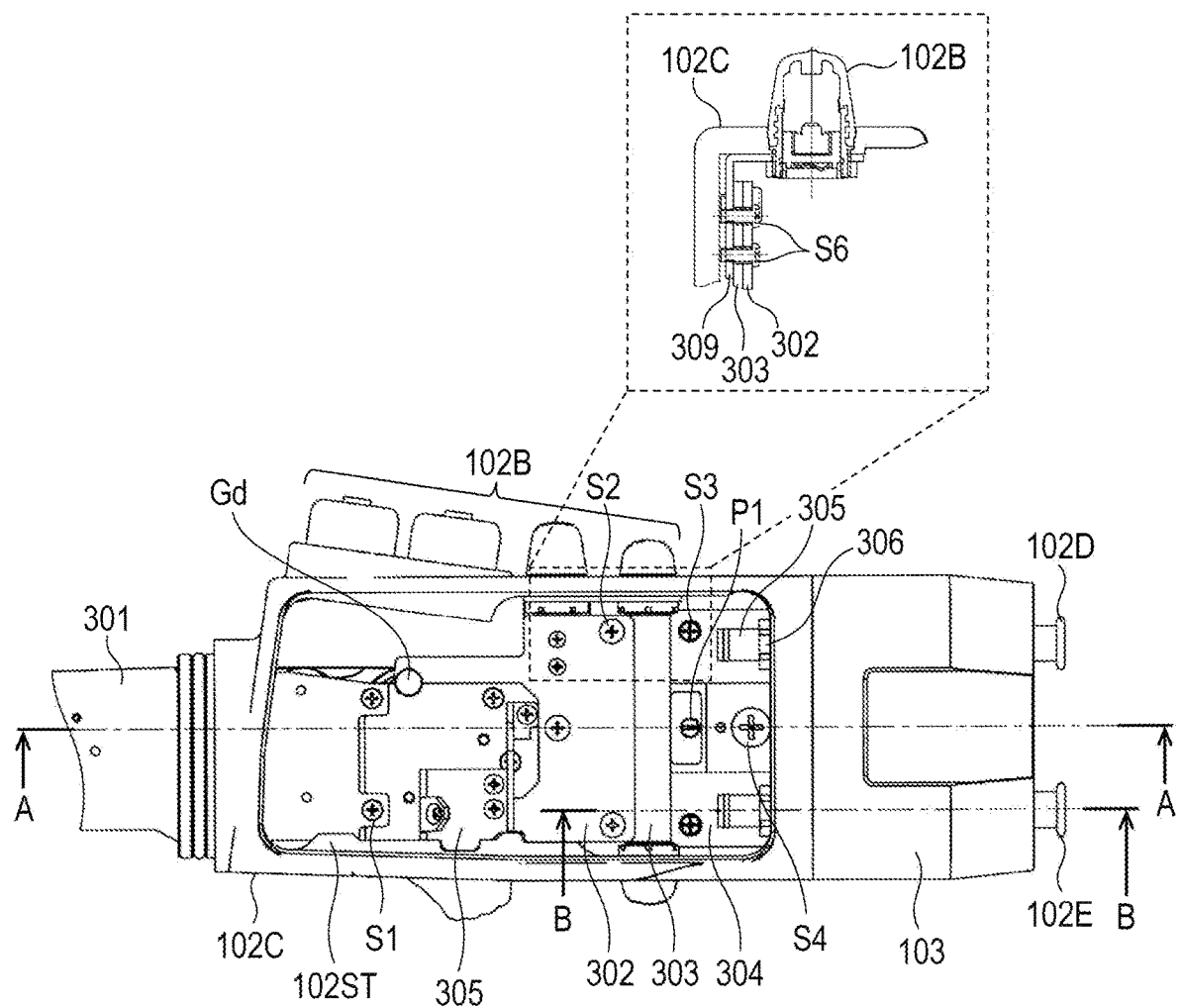
FIG. 4 is a plan view illustrating details of the structures of the hand operation unit 102 and the joint section 103.
Figure 5:
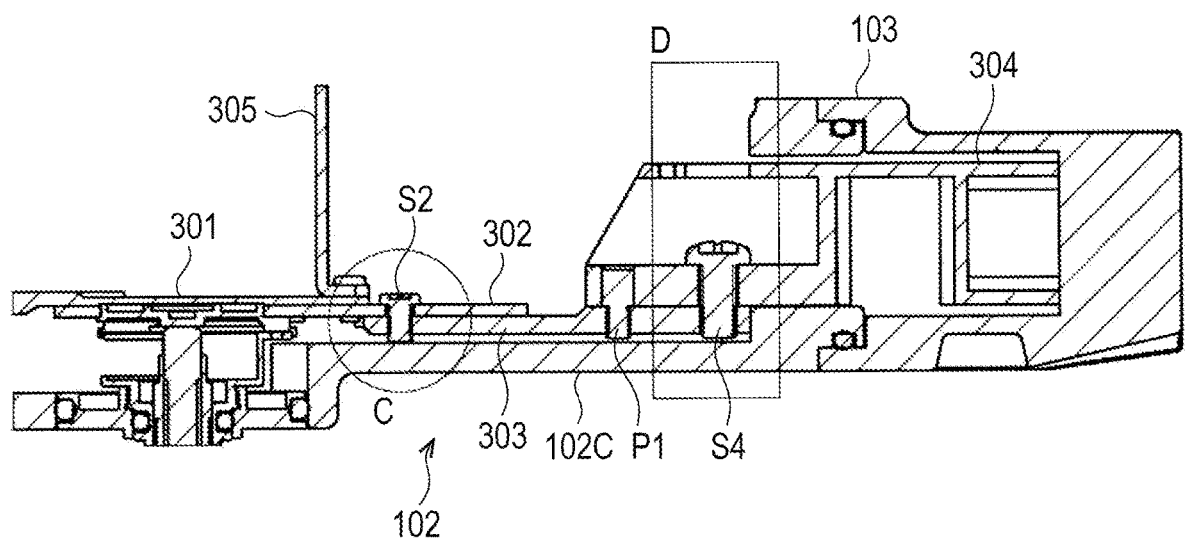
FIG. 5 is a cross-sectional view illustrating details of the structures of the hand operation unit 102 and the joint section 103.
Figure 6:
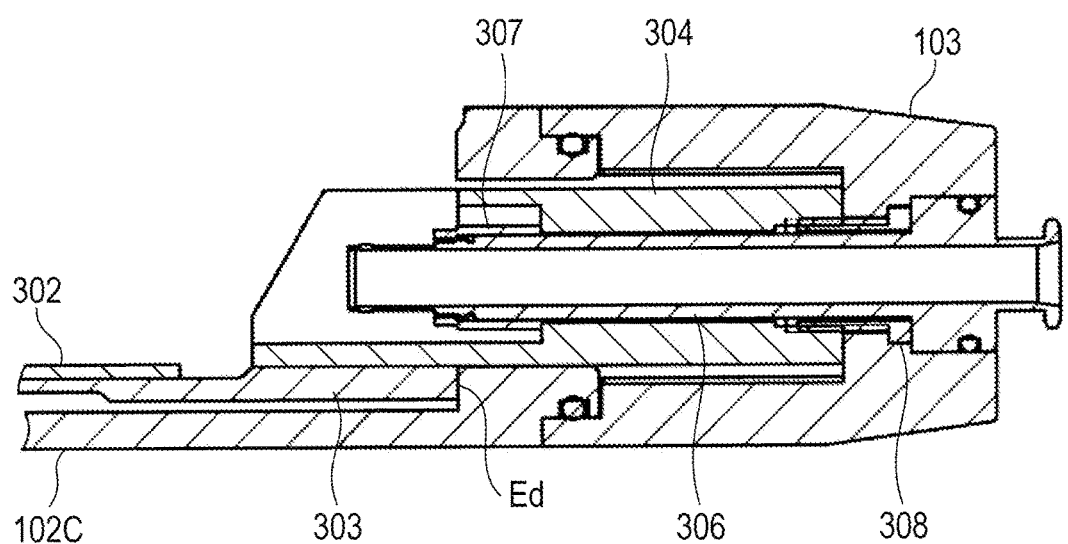
FIG. 6 is a cross-sectional view illustrating details of the structures of the hand operation unit 102 and the joint section 103.

Structures of the hand operation unit 102 and the joint section 103 will be described in detail with reference to FIGS. 3 to 6. FIG. 3 is a perspective view of the hand operation unit 102 and the joint section 103 and illustrates a state in which a part of a cover of the hand operation unit 102 has been removed. In addition, FIG. 4 is a plan view of the hand operation unit 102 and the joint section 103, and FIGS. 5 and 6 are cross-sectional views respectively taken along lines A-A and B-B in FIG. 4.

As illustrated in FIG. 3, plates 301 to 303 and a frame 304 are provided inside a case 102C constituting the hand operation unit 102 and the joint section 103. FIG. 3 illustrates only the plates 301 to 303 and the frame 304 among the internal configurations of the case 102C and the joint section 103, and does not illustrate the other components.

Each of the plates 301 to 303 has a substantially planar plate shape, but the plate 303 may have a rib structure extending along an arrangement direction of the treatment tool channels 119A to 119C as an example. In addition, the frame 304 includes a plurality of partition structural members having partitions which are coupled to each other and have a longitudinal direction along the arrangement direction of the treatment tool channels 119A to 119C as will be described later.

As will be described later, the plates 301 to 303 are coupled and fixed to each other by screws or the like, and the frame 304 is also coupled to the plate 303, whereby the frame 304 is arranged inside the joint section 103. Note that the plate 302 is also provided with a connection plate 305 extending in a direction substantially orthogonal to the plane of the plate 302. The connection plate 305 is a fixing member for connecting and fixing the universal cable 105 to the hand operation unit 102.

As illustrated in FIG. 4, the plate 301 is fixed to the plate 302 using a plurality of screws S1. In addition, the plate 302 is fixed to the plate 303 using a plurality of screws S2. In addition, the plate 303 is positioned with respect to the frame 304 using the alignment pins P1 and is fixed using two screws S3 and one S4. Then, the joint section 103 is fixed to the frame 304 by means to be described later. Note that the plates 302 and 303 are fixed to the case 102C by an L-shaped fixation 309 extending from the operation button 102B and a screw S6 as illustrated in an enlarged manner in FIG. 4.

In this manner, the case 102C and the joint section 103 are fixed to the plates 301 to 303 and the frame 304. Note that the plates 301 to 303 and the frame 304 may be made of aluminum or stainless steel. Note that the case 102C is provided with a stopper 102ST for preventing the plates 301 to 303 from moving in a direction perpendicular to the plane.

FIG. 6 is a cross-sectional view taken along line B-B in FIG. 4, and illustrates a state of the connection of the joint section 103 with respect to the frame 304 and the plate 303. As illustrated in FIG. 6, the case 102C has a protrusion Ed at an end portion on the joint section 103 side, and the plate 303 is positioned with respect to the case 102C by arranging the plate 303 such that one end of the plate 303 is in contact with this protrusion Ed. On the other hand, the joint section 103 is mounted onto the frame 304 fixed to the plate 303 (fixed using a fixing ring 308 to be described later).

Figure 7:
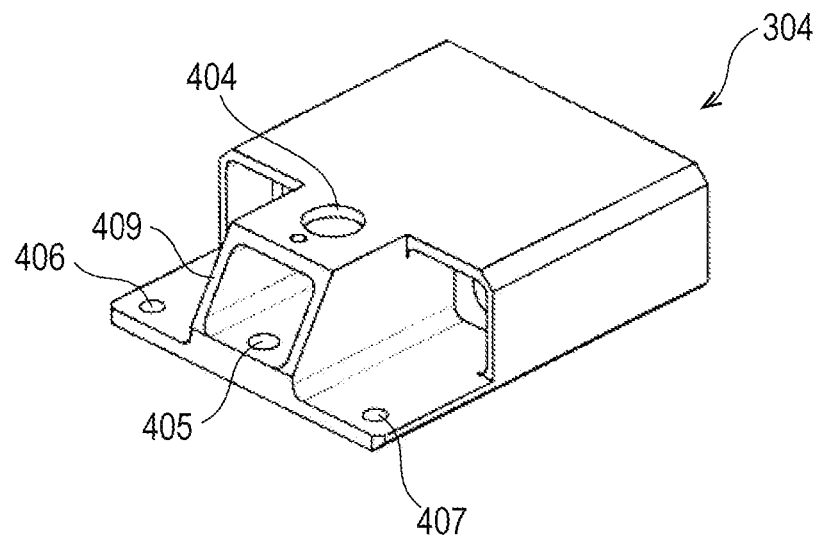
FIG. 7 is a perspective view illustrating an example of a structure of a frame 304.
Figure 8:
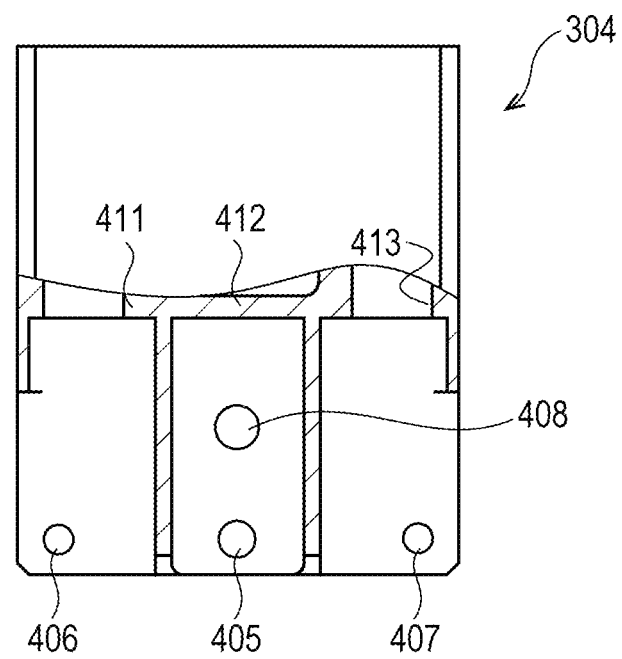
FIG. 8 is a plan view illustrating an example of the structure of the frame 304.
Figure 9:
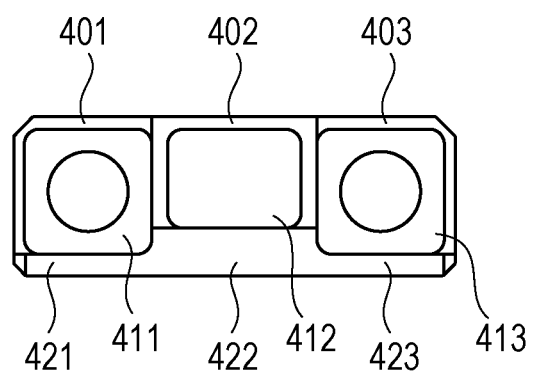
FIG. 9 is a front view illustrating an example of the structure of the frame 304.
Figure 10:
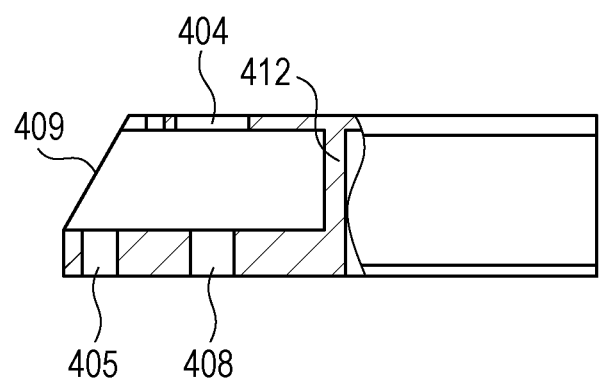
FIG. 10 is a cross-sectional view illustrating an example of the structure of the frame 304.

An example of a structure of the frame 304 will be described with reference to FIGS. 7 to 10. FIG. 7 is a perspective view illustrating the structure of the frame 304, and FIGS. 8, 9, and 10 are a plan view, a front view, and a cross-sectional view of a lower surface (bottom plate) of the frame 304, respectively. As illustrated in FIG. 9, the frame 304 is configured by arraying a plurality of (for example, three) hollow partition structural members 401 to 403 each of which is formed in a rectangular box-shaped shape and has a longitudinal direction along the arrangement direction (longitudinal direction) of the treatment tool channels 119A to 119C in parallel. With such a partition structure, the frame 304 has sufficient mechanical strength against a tensile direction, a rotational direction, and sway.

The central partition structural member 402 located between the partition structural members 401 and 403 has a through-hole 404 on its upper surface. As illustrated in FIG. 8, a screw hole 408 for the screw S4 is provided in a lower surface immediately below the through-hole 404. In addition, a pin hole 405 into which the alignment pin P1 is inserted is provided at a position at the front of the screw hole 408.

An end surface on the front side of the partition structural member 402 is an inclined portion 409 having a predetermined inclination with respect to the lower surface in order to facilitate insertion of the alignment pin P1 into the pin hole 405. That is, the inclined portion 409 is provided in the vicinity of the pin hole 405. In addition, an interior side surface 412 blocking a hollow portion is provided in the hollow portion of the partition structural member 402 as illustrated in FIG. 10. This interior side surface 412 contributes to improvement in mechanical strength of the partition structural member 402.

In addition, the partition structural members 401 and 403 on both left and right sides include interior side surfaces 411 and 413, respectively, as illustrated in FIGS. 8 and 9. This interior side surface 411 and 413 also contribute to improvement in mechanical strength of the partition structural members 401 and 403, which is similar to the interior side surface 412.

In addition, the partition structural members 401 and 403 include a sleeve 306 for connecting the treatment tool channels 119B and 119C therein. The sleeve 306 penetrates the interior side surfaces 411 and 413 and is fixed to an end surface of the frame 304, specifically, the interior side surfaces 411 and 413 by a fixing ring 307. The frame 304 is fixed by the fixing ring 308 at an end surface of the joint section 103 so that the joint section 103 and the sleeve 306 are fixed to the frame 304. Note that, regarding thicknesses of lower surfaces of the partition structural members 401 to 403, the thickness of a lower surface 422 of the central partition structural member 402 is larger than the thicknesses of lower surfaces 421 and 423 of the left and right partition structural members 401 and 403 (see FIG. 9). In a case where a force is applied to the hand operation unit 102 in the rotational direction in a state where the joint section 103 is mounted on the hanger 104, a portion to which the load is applied the most is a portion of the screw S4. Therefore, the strength of the frame 304 can be improved by increasing the thickness of the lower surface 422 of the partition structural member 402. Note that it is preferable to use a screw larger than screws used for the lower surfaces 421 and 423 as the screw used for the thick lower surface 422 of the partition structural member 402.

In addition, the partition structural members 401 and 403 on the left and right sides have screw holes 406 and 407 for insertion of the above-described screw S3 at end portions of the lower surfaces thereof, respectively. Note that the screw holes 406 and 407 may be provided at any positions, and are preferably arranged to form an isosceles triangle with the screw hole 408 for the screw S4. In addition, in the structure example illustrated in FIG. 7, upper surfaces of the partition structural members 401 and 403 on the left and right sides have end portions at positions retracted from that of the partition structural member 402 in order to facilitate screwing of the screw S3 into the screw holes 406 and 407. Meanwhile, it is also possible to provide the end portions of the upper surfaces on the front surface side by providing through-holes similar to the through-hole 404 on the upper surfaces as in the partition structural member 402.

Figure 11:
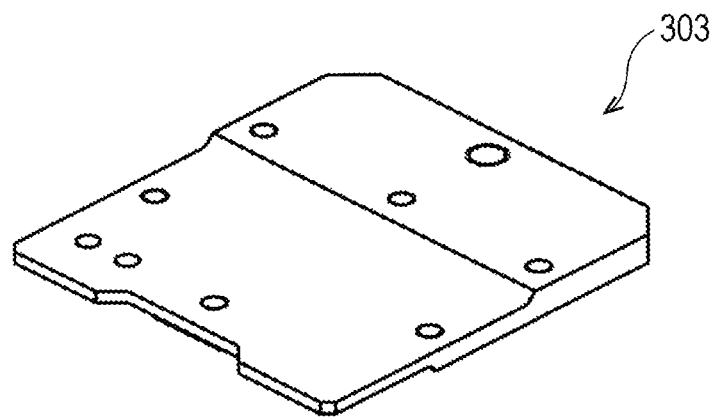
FIG. 11 is a perspective view illustrating an example of a structure of a plate 303.
Figure 12:
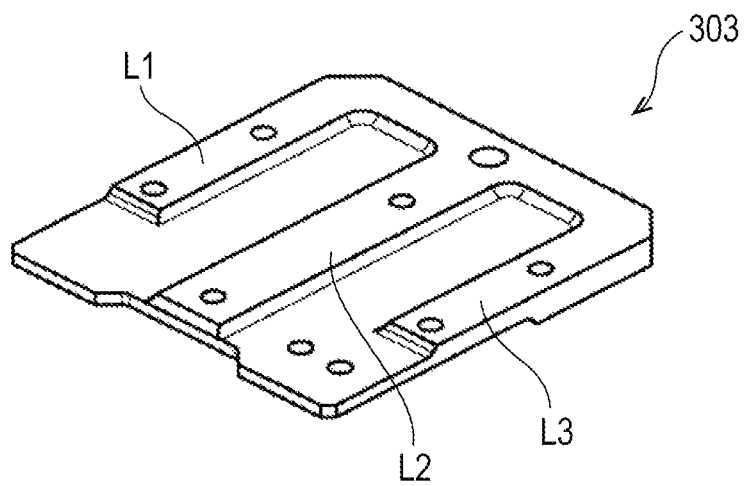
FIG. 12 is a perspective view illustrating an example of the structure of the plate 303.

An example of a structure of the plate 303 will be described with reference to FIGS. 11 and 12. FIG. 11 is a perspective view in which the upper surface side of the plate 303 faces upward, and FIG. 12 is a perspective view in which the lower surface side faces upward. As illustrated in FIG. 12, the plate 303 has a rib structure including ribs L1 to L3 which extend along the longitudinal direction of the channel. The plate 303 having the rib structure and the frame 304 in which the plurality of partition structural members 402 are coupled provide the hand operation unit 102 with high mechanical strength so that high reliability can be obtained. Note that the side surface of the partition structural member of the frame 304 can contribute to improvement in strength in the tensile direction similarly to the rib structure.

Figure 13:
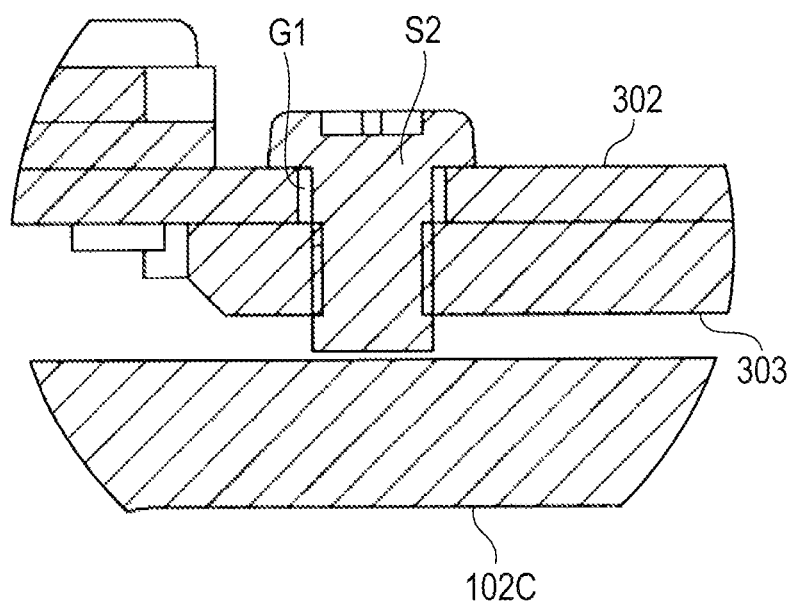
FIG. 13 is a cross-sectional view of the vicinity of a mounting portion of a screw S2.

Note that the plate 302 includes a position adjustment space G1 in a screw hole of screw S2 for fixing the plate 303 as illustrated in FIG. 13 (an enlarged view of the vicinity of reference sign C in FIG. 5). The position adjustment space G1 facilitates mounting of the plate 303 regardless of variations in size between products regarding the frame 304 and the plate 302 positioned by the alignment pin P1.

Figure 14:
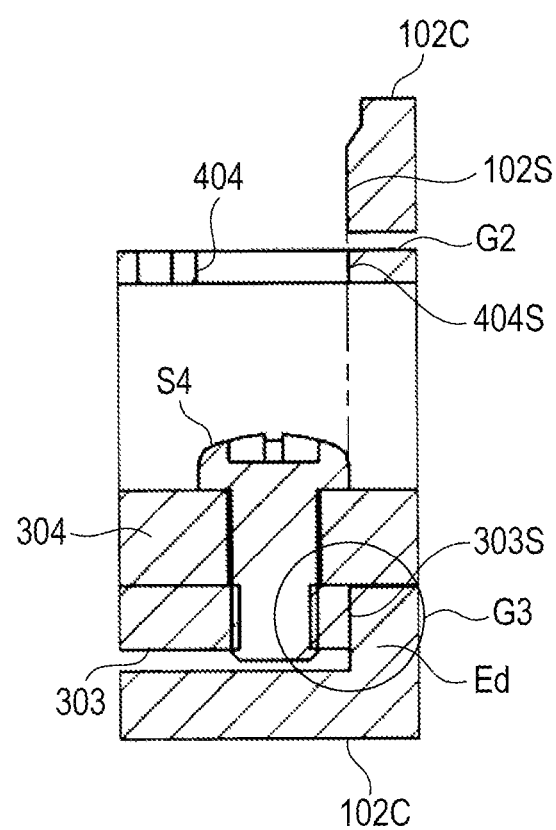
FIG. 14 is a cross-sectional view of the vicinity of a mounting portion of a screw S4.

In addition, the protrusion Ed is provided at the end portion of the case 102C, and one end 303S of the plate 303 abuts against an inner surface thereof as illustrated in FIG. 14 (an enlarged view of the vicinity of reference sign D in FIG. 5). The plate 303 and the frame 304 are positioned with respect to the case 102C by the abutment of the end portion 303S against the protrusion Ed and the insertion of the alignment pin P1. An end surface 404S of the through-hole 404 is preferably formed so as to match an end surface 102S of the case 102C in order to improve the mounting property of the screw S4.

[Others]

The present invention is not limited to the above-described examples, and includes various modified examples. For example, the above-described examples have been described in detail for the purpose of facilitating understanding of the present invention, and are not necessarily limited to those including all the described configurations. In addition, a part of the configuration of a certain example can be replaced with a configuration of another example, and the configuration of the another example can be added to the configuration of the certain example. In addition, it is possible to add, delete, and replace another configuration for a part of the configuration of each of the examples.

REFERENCE SIGNS LIST 100 endoscope
101 insertion portion
1011 distal tip
1012 bending section
1013 flexible tube section
102 hand operation unit
102A bending adjustment knob
102B operation button
102C case
103 joint section
104 hanger
105 universal cable
106 connector unit
112A, 112B light distribution lens
113 objective lens
114 air/water supply port
115 auxiliary water supply port
116A to C treatment tool port
117 image sensor
118 electrical wiring
119A to C treatment tool channel
200 master system
202 input device
203 display
204 controller
211 processor
212 air/water supply unit
213 suction unit
214 motor box
215 processor for master slave system
216 display
301 to 303 plate
304 frame 305 connection plate
306 sleeve
307, 308 fixing ring

The invention claimed is:

1. An endoscope device comprising:
an insertion portion;
an operation unit that has a joint section configured to be suspendable on a hanger and is connected to the hanger through the joint section;
a treatment tool channel that is arranged inside the joint section and the operation unit and allows passage of a treatment tool;
a plate fixed to the operation unit; and
a frame that is provided inside the joint section, includes a plurality of partition structural members coupled to each other and having a longitudinal direction along an arrangement direction of the treatment tool channel, and is fixed to the plate, wherein:
one partition structural member of the plurality of partition structural members is arranged in parallel at a position sandwiched between other partition structural members, and
a thickness of a bottom plate of the one partition structural member is larger than thicknesses of bottom plates of the other partition structural members.

2. The endoscope device according to claim 1, wherein the frame has a screw hole for a screw configured to fix the frame to the plate.

3. The endoscope device according to claim 1, wherein the frame includes a pin hole for allowing insertion of an alignment pin configured to align the frame with the plate.

4. The endoscope device according to claim 1, wherein each of the plurality of partition structural members has a rectangular box shape.

5. The endoscope device according to claim 1, wherein the plurality of partition structural members are arrayed in parallel with the longitudinal direction.

6. The endoscope device according to claim 1, wherein the one partition structural member has a through-hole in an upper surface and has a screw hole for fixing the frame to the plate below the through-hole.

7. The endoscope device according to claim 1, wherein the one partition structural member has an inclined portion, inclined with respect to a lower surface, at an end portion on a side close to the operation unit, and has a pin hole for allowing passage of a positioning pin in the lower surface corresponding to a position of the inclined portion.

8. The endoscope device according to claim 1, wherein the plate has a rib structure including a rib extending along the arrangement direction of the treatment tool channel.

* * * * *